(12) United States Patent
Haider et al.

(10) Patent No.: US 8,876,715 B2
(45) Date of Patent: Nov. 4, 2014

(54) METHOD AND SYSTEM FOR CORRECTING ULTRASOUND DATA

(75) Inventors: Bruno Hans Haider, Ballston Lake, NY (US); Kenneth Wayne Rigby, Clifton Park, NY (US); Jean-Francois Gelly, Sophia-Antipolis (FR); Kjell Kristoffersen, Oslo (NO); Alexander Sokulin, Kiryat Tivon (IL)

(73) Assignee: General Electric Company, Niskayuna, NY (US)

( * ) Notice: Subject to any disclaimer, the term of this patent is extended or adjusted under 35 U.S.C. 154(b) by 974 days.

(21) Appl. No.: 12/950,238

(22) Filed: Nov. 19, 2010

(65) Prior Publication Data

US 2012/0130246 A1    May 24, 2012

(51) Int. Cl.
*A61B 8/00* (2006.01)
*G03B 42/06* (2006.01)
*A61B 8/08* (2006.01)
*G01S 7/52* (2006.01)
*G01S 15/89* (2006.01)

(52) U.S. Cl.
CPC .............. *G03B 42/06* (2013.01); *A61B 8/5269* (2013.01); *G01S 7/5205* (2013.01); *G01S 15/8915* (2013.01); *A61B 8/4488* (2013.01); *A61B 8/4477* (2013.01)
USPC ............ 600/437; 600/459; 600/463; 600/585

(58) Field of Classification Search
USPC .................................. 600/437, 459, 463, 585
See application file for complete search history.

(56) References Cited

U.S. PATENT DOCUMENTS

| 4,407,693 | A | 10/1983 | Paquin |
| 4,676,251 | A | 6/1987 | Bernatets |
| 5,846,204 | A | 12/1998 | Solomon |
| 6,117,083 | A | 9/2000 | Buck et al. |
| 6,559,389 | B1 | 5/2003 | Kornrumpf et al. |
| 6,734,362 | B2 | 5/2004 | Buck et al. |
| 2005/0061536 | A1 | 3/2005 | Proulx |

FOREIGN PATENT DOCUMENTS

CN           1259666 A       7/2000

OTHER PUBLICATIONS

Griffith et al., "Electrical Characteristics of Ribbon-based Probe cables", IEEE Ultrasonics Symposium Proceedings, vol. 2, pp. 1085-1090, Oct. 17-20, 1999, Caesars Tahoe, NV , USA.

Griffith et al., "Crosstalk in Ribbon-based Probe Cables", IEEE Ultrasonics Symposium, vol. 2, pp. 1143-1148, Oct. 22-25, 2000,San Juan , Puerto Rico.

Oakley et al., "A Minimally Invasive Ultrasound Probe using Non-coax Cabling", IEEE Ultrasonics Symposium, vol. 2, pp. 1011-1016, Oct. 7-10, 2001,Atlanta, GA , USA.

(Continued)

*Primary Examiner* — Joel Lamprecht
(74) *Attorney, Agent, or Firm* — Eileen B. Gallagher

(57) ABSTRACT

A method for correcting ultrasound data includes acquiring ultrasound data using an ultrasound probe having a plurality of transducer elements associated with a plurality of channels that include conductive pathways and communicating the ultrasound data as received ultrasound signals along the conductive pathways of the channels. The method further includes determining a crosstalk signal that is generated in one or more of the channels by at least one of communication of the received ultrasound signals along the channels or vibration of one or more of the transducer elements. In one aspect, the method also includes modifying one or more subsequently acquired ultrasound signals that are communicated along the channels based on the crosstalk signal.

20 Claims, 10 Drawing Sheets

(56) References Cited

OTHER PUBLICATIONS

Oakley et al., "5E-4 A Matrix Method for Modeling Electrical Crosstalk Applied to Ultrasonic Imaging Probes Using Micro-Miniature Ribbon Cable", IEEE Ultrasonics Symposium, pp. 480-484, Oct. 2-6, 2006, Vancouver, BC.

Chinese Office Action issued in connection with corresponding CN Application No. 201110385263.5 on Aug. 18, 2014.

us 8,876,715 B2

METHOD AND SYSTEM FOR CORRECTING ULTRASOUND DATA

BACKGROUND OF THE INVENTION

The subject matter disclosed herein relates generally to ultrasound systems, and more particularly to methods and systems for processing data within an ultrasound system, such as data transferred from a front end of the ultrasound system to a back end for processing.

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging a volume or body). The ultrasound systems are controllable to operate in different modes of operation and to perform different scans. The signals received at the front end of the ultrasound system are then communicated to and processed at a back end.

In some known ultrasound systems, coaxial cables electrically couple the probe to the front and back ends of the system. The coaxial cables can include conductive wires enclosed in insulative layers with an additional conductive shield coaxially disposed around the insulative layers. The cables separately transmit ultrasound data that is used to form ultrasound images. Coaxial cables are used to reduce crosstalk and other signals being induced between nearby or neighboring cables. Crosstalk and induced signals can degrade the quality of the ultrasound images. For example, crosstalk between non-coaxial cables can create spurious ultrasonic echoes that may obscure low echogenic regions of an imaged body.

Currently used coaxial cables have numerous shortcomings. For example, the cables can be relatively heavy and stiff, thereby decreasing their maneuverability by sonographers. The sonographers also must exert effort to move the ultrasound probes that are joined to the cables. This effort can result in repetitive strain injuries for sonographers.

Moreover, the vibration of one transducer element in the probe may induce crosstalk signals, or mechanical crosstalk signals, on another transducer element. The mechanical crosstalk signals can degrade image quality.

BRIEF DESCRIPTION OF THE INVENTION

A method for correcting ultrasound data includes acquiring ultrasound data using an ultrasound probe having a plurality of transducer elements associated with a plurality of channels that include conductive pathways and communicating the ultrasound data as received ultrasound signals along the conductive pathways of the channels. The method further includes determining a crosstalk signal that is generated in one or more of the channels by at least one of communication of the received ultrasound signals along the channels or vibration of one or more of the transducer elements. In one aspect, the method also includes modifying one or more subsequently acquired ultrasound signals that are communicated along the channels based on the crosstalk signal.

In another embodiment, an ultrasound system is provided. The system includes an ultrasound probe, a plurality of channels associated with the probe, and a processor. The probe is configured to acquire ultrasound echoes and transmit ultrasound signals based on the ultrasound echoes. The channels include conductive pathways that are configured to communicate the ultrasound signals. The processor is communicatively coupled with the channels and monitors the channels to determine a crosstalk signal that is induced on one or more of the conductive pathways of the channels by communication of the ultrasound signals along the conductive pathways. In one embodiment, the processor modifies one or more subsequently acquired ultrasound signals that are communicated along the conductive pathways based on the crosstalk signal.

In another embodiment, a tangible computer readable storage medium for an ultrasound system having a processor and an ultrasound probe associated with a plurality of channels over which ultrasound signals are communicated is provided. The computer readable storage medium includes instructions to direct the ultrasound probe to acquire ultrasound data and communicate the ultrasound data along the channels as ultrasound signals. The medium also includes instructions to direct the processor to determine a crosstalk signal that is induced on one or more conductive pathways associated with the channels by communication of the ultrasound signals along the conductive pathways. In one aspect, the instructions direct the processor to modify one or more of the ultrasound signals communicated along the conductive pathways based on the crosstalk signal.

DETAILED DESCRIPTION OF THE INVENTION

Figure 1:
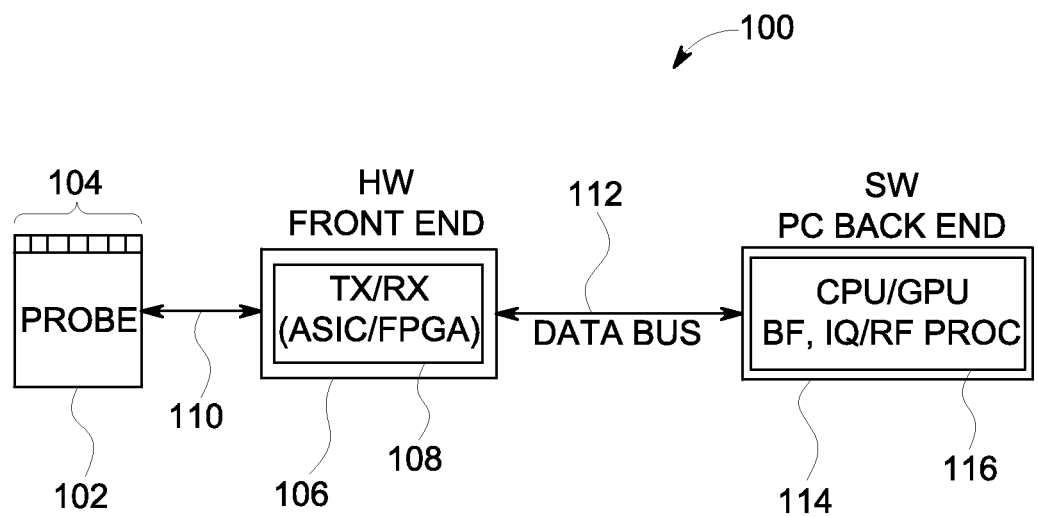
FIG. 1 illustrates a simplified block diagram of an ultrasound system in accordance with one embodiment.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

One or more embodiments described herein provide a system and method for communicating data within an ultrasound system and/or for processing the data. In one embodiment, the system and method determines and corrects for electric irregularities and/or deficiencies of the ultrasound system that may negatively impact acquired ultrasound data. For example, the system and method can determine crosstalk signals that are induced on one pathway (an "induced pathway") associated with one channel (an "induced channel") by another, different pathway (an "inducing pathway") that is associated with another, different channel (an "inducing channel"). The crosstalk signals can include electrical and/or mechanical crosstalk signals. For example, with respect to electrical crosstalk, the ultrasound signals that are electrically conveyed along the inducing pathway for the inducing channel may create electrical crosstalk signals on the induced pathway for the induced channel. With respect to mechanical crosstalk, the vibration of one transducer element (an "inducing element") that is associated with the inducing pathway and inducing channel may induce a mechanical crosstalk signal on another, different transducer element (an "induced element") that is associated with the induced pathway and induced channel. The term "channel" can refer to the entire pathway communicating a single analog ultrasound signal. The pathway for a particular channel may include the transducer element, electrical interconnect, analog signal processing, if any, in the probe, the electrical cabling connecting the probe and the system console, the cable connector, and the receive analog circuitry in the console.

The system and method identifies the crosstalk signals to correct the ultrasound data communicated using the induced channel to remove the crosstalk signals from the ultrasound data and thereby improve imaging or other diagnostic quality. In one embodiment, the determination and correction of the ultrasound signals that include the ultrasound data is performed on raw analog ultrasound data, such as ultrasound data that is acquired but otherwise unprocessed and/or unable to be visually presented on a display device without further processing. The determination and correction of the electric signals can be performed by one or more software applications or modules rather than in beamforming hardware.

A technical effect of at least some embodiments includes improving the imaging and/or diagnostic quality of acquired ultrasound data while permitting less cumbersome, lighter, and/or more flexible cables to be used to couple the ultrasound probe with the ultrasound system. For example, in conjunction with one or more embodiments described herein, non-coaxial cables may be used to communicate the ultrasound data from the probe to a processor, such as a computer microprocessor, while avoiding significant degradation to the ultrasound data due to crosstalk between the wires in the cable and/or transducer elements in the probe.

It should be noted that the various embodiments described herein that generate or form images may include processing for forming images that in some embodiments include beamforming and in other embodiments do not include beamforming. For example, an image can be formed without beamforming, such as by multiplying the matrix of demodulated data by a matrix of coefficients so that the product is the image, and wherein the process does not form any "beams." Also, forming of images may be performed using channel combinations that may originate from more than one transmit event.

FIG. 1 illustrates a simplified block diagram of an ultrasound system 100 in accordance with one embodiment. In various embodiments described herein, ultrasound processing to form images is performed in software, hardware, or a combination thereof. The illustrated embodiment of the ultrasound system 100 implements a software-based beamformer architecture. Alternatively, the ultrasound system 100 may have a beamformer that is at least partially implemented in hardware. The ultrasound system 100 acquires ultrasound data using an ultrasound probe 102 having multiple transducer elements 104. The ultrasound probe 102 transmits ultrasound pulses and/or receives ultrasound echoes of the ultrasound pulses off of imaged objects using the transducer elements 104. In one embodiment, the transducer elements 104 represent individual transducer elements. Alternatively, the transducer elements 104 may represent groups or sets of individual transducer elements, such as a subaperture of transducer elements. A front end 106 of the ultrasound system controls transmission of pulses and reception of echoes by the transducer elements 104. The front end 106 may include a hardware implemented transmit and/or receive beamformer (not shown) that performs partial or complete beamforming of the received echoes. The front end 106 generally includes a transmitter/receiver 108, which may be implemented in, for example, an application specific integrated circuit (ASIC) or a field-programmable gate array (FPGA).

The probe 102 is coupled with the front end 106 by one or more cables 110. By way of example only, the cable 110 can include several non-coaxial wires, such as several conductive wires that are not independently or separately shielded with respect to each other. The ultrasound data that is acquired by the probe 102 is conveyed from the probe 102 to other components of the ultrasound system 100 over a plurality of channels. As described above, the channels may represent the signal paths that ultrasound signals are conveyed. The channels may be associated with different transducer elements 104 of the probe 102 and different wires, busses, and the like, used to convey the ultrasound signals from the probe 102 to other components of the system 100. The cable 110 also communicates transmit signals, such as control signals, from the front end 106 to the probe 102. The transducer elements 104 are controlled by the transmit signals to emit ultrasound pulses into an imaged body.

The ultrasound signals are communicated over the channels to a back end 114 through a data bus 112 that connects the front and back ends 106, 114. The back end 114 generally includes one or more processors 116, such as processing units that include a software implemented beamformer, an IQ/RF processor, a general purpose CPU, and/or a graphics processing unit (GPU).

The ultrasound system 100 may be used to perform different kinds of ultrasound scans for different applications to acquire ultrasound image data. For example, in some embodiments, the ultrasound system 100 operates to perform real-time four-dimensional (4D) scanning that acquires multiple beams simultaneously or concurrently. The ultrasound system 100 includes the software implemented beamformer provided via a general purpose processor (e.g., CPU or GPU) that receives data from the channels of the cable 110. In one embodiment, the ultrasound data is communicated over all or substantially all of the channels of the cable 110 with the general purpose processor 116 performing beamforming processing, such as beamforming calculations using any suitable beamforming method. It should be noted that software beamforming can include performing any type of beamforming technique, which may include performing beamforming techniques in software that can be performed in hardware. It also should be noted that when reference is made herein to beamforming techniques, this generally refers to any type of image forming that may be performed by the ultrasound system. Accordingly, the various embodiments may be implemented in connection with forming images whether or not beams are formed.

Figure 2:
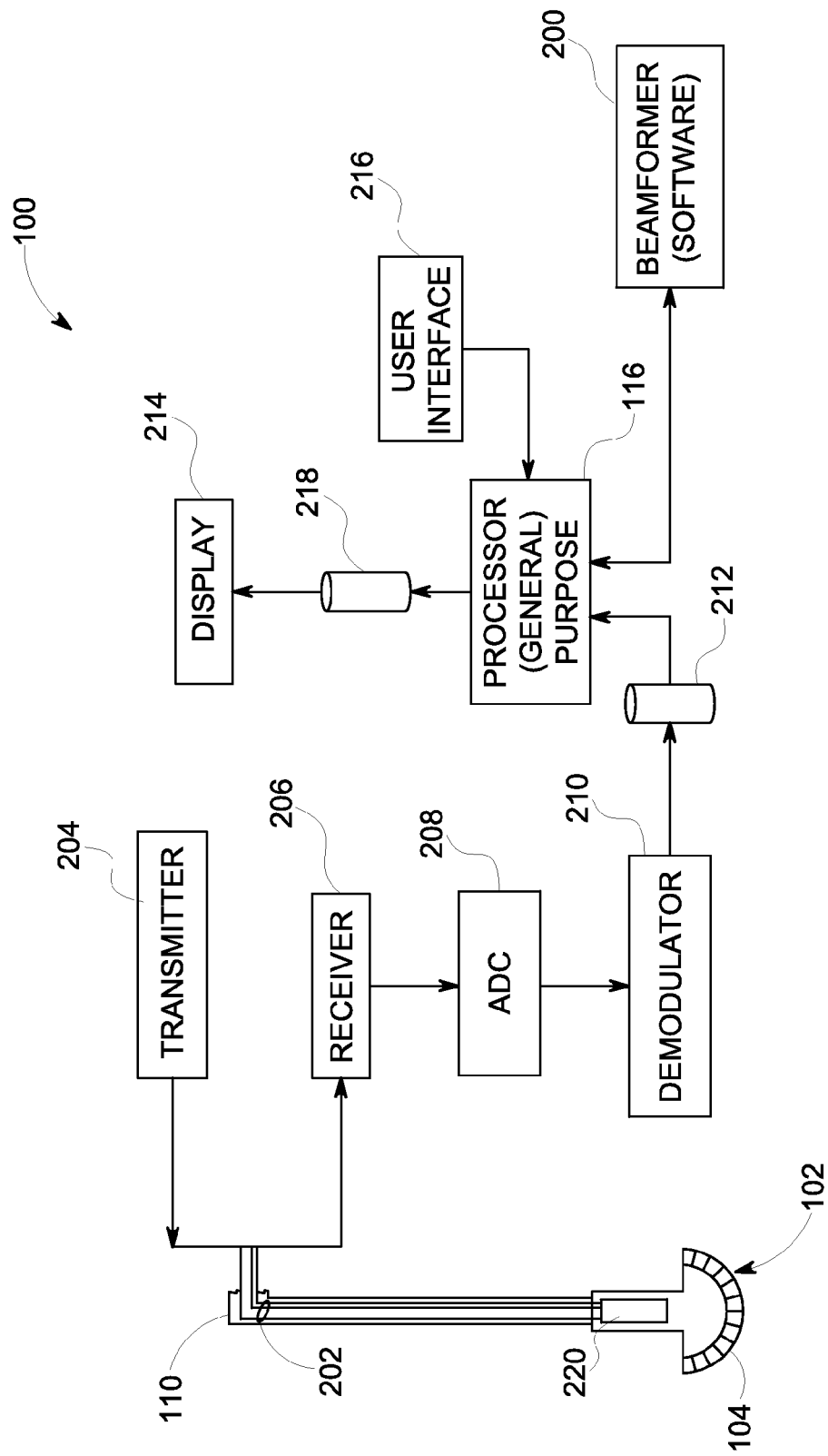
FIG. 2 is a detailed block diagram of the ultrasound system in accordance with one embodiment.

FIG. 2 is a detailed block diagram of the ultrasound system 100 in accordance with one embodiment. The ultrasound system 100 shown in FIG. 1 illustrates additional components of the ultrasound system 100. The ultrasound system 100 performs software beamforming using, for example, the processor 116 executing instructions on a tangible, non-transitory computer readable storage medium, such as an internal memory 212. The term "non-transitory" means that the internal memory 212 is not a transient electrical signal, such as a transmitted electric signal that is not stored in a medium for any period of time. The internal memory 212 may include volatile and/or non-volatile storage media. For example, the memory 212 may include an electrically erasable programmable read only memory (EEPROM), a simple read only memory (ROM), programmable read only memory (PROM), erasable programmable read only memory (EPROM), random access memory (RAM), or computer hard drive.

The ultrasound system 100 is capable of electrical or mechanical steering of a soundbeam (such as in 3D space) and is configurable to acquire information corresponding to a plurality of 2D representations or images (or optionally 3D and 4D images) of a region of interest (ROI) in a subject or patient, which may be defined or adjusted as described in more detail herein. The ultrasound system 100 is configurable to acquire 2D images, for example, in one or more planes of orientation.

The ultrasound system 100 is configured to acquire ultrasound data using the probe 102. The probe 102 is connected to the other electronic components of the ultrasound system 100 by the cable 110, which includes several conductive pathways 202. The acquired ultrasound data is communicated through the conductive pathways 202 as ultrasound signals. Other signals, such as control signals that direct the transducer elements 104 of the probe 102 to excite and transmit ultrasound waves along various directions, also may be communicated through the conductive pathways 202. As described above, the channels over which ultrasound signals are conveyed include the signal path comprised of the conductive pathways 202 and/or the associated transducer elements 104. Additionally, the signal paths may include additional components or media over which the ultrasound signals are conveyed from the transducer elements 104 to one or more processing components of the system 100. At least some of the processing of the analog ultrasound signals that are acquired by the probe 102 may be performed by components disposed within the probe 102 and/or outside of the probe 102.

In the illustrated embodiment, the ultrasound system 100 includes a signal generator 220 that is electrically coupled with the channels over which ultrasound signals are conveyed. For example, the signal generator 220 may be electrically interconnected with the conductive pathways 202 of the cable 110. The signal generator 220 is a device that generates test signals that are transmitted along the conductive pathways 202 in order to identify crosstalk between the conductive pathways 202. The signal generator 220 may include, or be composed of, a processor or other logic-based device, such as a microcontroller. The signal generator 220 may differ from the transmitter 204 or the beamformer 200 in that the signal generator 220 may not generate signals that drive the transducer elements 104 to emit ultrasound waves used to image a body or object.

The conductive pathways 202 of the cable 110 are unshielded, non-coaxial wires or filars in one embodiment. For example, the conductive pathways 202 may be wires that are electrically insulated from each other (such as by insulative outer jackets), but are not independently shielded relative to each other. By "not independently shielded," it is meant that each conductive pathway 202 does not have a shield electrically coupled to a ground reference that is separate from the shields of other conductive pathways 202. Examples of the cable 110 include a ribbon cable having several conductive pathways 202 held therein in an approximately coplanar relationship or a cable having several loosely packed wires. Alternatively, the cable 110 may include coaxial cables or wires, but have a stiffness or resistance to bending that is less than or equal to that of coaxial cables having the same or similar gauges.

The ultrasound system 100 includes a transmitter 204 that, under the guidance of a transmit beamformer (such as the software-based beamformer 200 or a hardward-based beamformer), drives an array of the transducer elements 104 (for example, piezoelectric elements) of the probe 102 to emit pulsed and/or continuous ultrasound waves into a body. A variety of geometries of the transducer elements 104 may be used. The ultrasound waves are back-scattered from structures in the body, like blood cells or muscular tissue, to produce echoes that return to and are received by the transducer elements 104. The echoes are communicated as ultrasound data from the transducer elements 104 to a receiver 206. In one embodiment, the echoes are communicated as analog signals to the receiver 206. The transducer elements 104 are mechanically coupled such that vibration of a first transducer element 104 induces a mechanical crosstalk signal on a second transducer element 104.

The ultrasound system 100 includes an analog-to-digital converter (ADC) 208 and a demodulator 210 in the illustrated embodiment. The ADC 208 and demodulator 210 may be different components or implemented in a single component, for example, in an application specific integrated circuit (ASIC). The ADC 208 receives acquired raw analog ultrasound data from the probe 102 and digitizes the raw analog ultrasound data into acquired raw digitized ultrasound data. The demodulator 210 may perform digital demodulation, filtering, and/or decimation of the raw analog ultrasound data. The ultrasound data is communicated to, and may be stored in, the internal memory 212. Accordingly, the raw data may be modified or compensated in addition to being beamformed.

The processor 116 is adapted to perform one or more processing operations according to a plurality of selectable ultrasound modalities on the acquired ultrasound data. The processor 116 also performs beamforming operations using the software-implemented beamformer 200 in the illustrated embodiment. The beamformer 200 shown connected to the processor 116 may be software running on the processor 116 or hardware provided as part of the processor 116. The processor 116 processes the acquired ultrasound data and prepares frames of ultrasound information for visual presentation on a display device 214. The processor 116 also determines operational characteristics of ultrasound data (such as crosstalk signals) and modifies the ultrasound data to filter, remove, or reduce the operational characteristics, such as mechanical and/or electric crosstalk signals, form the ultrasound data.

The display device 214 includes one or more monitors that present patient information, including diagnostic ultrasound images to the user for diagnosis and analysis. The processor 116 is connected to a user interface 216 (which may include a mouser, keyboard, etc.) that may control operation of the processor 116. One or both of the memory 212 and an external memory 218 may store two-dimensional (2D) or three-dimensional (3D) data sets of the ultrasound data, where such 2D and 3D data sets are accessed to present 2D (and/or 3D or 4D images), which may be in different states of beamforming. The images may be modified and the display settings of the display device 214 also manually adjusted using the user interface 216.

It should be noted that although the various embodiments may be described in connection with an ultrasound system, the methods and systems are not limited to ultrasound imaging or a particular configuration thereof. The various embodiments may be implemented in connection with different types of imaging systems, including, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

Figure 3:
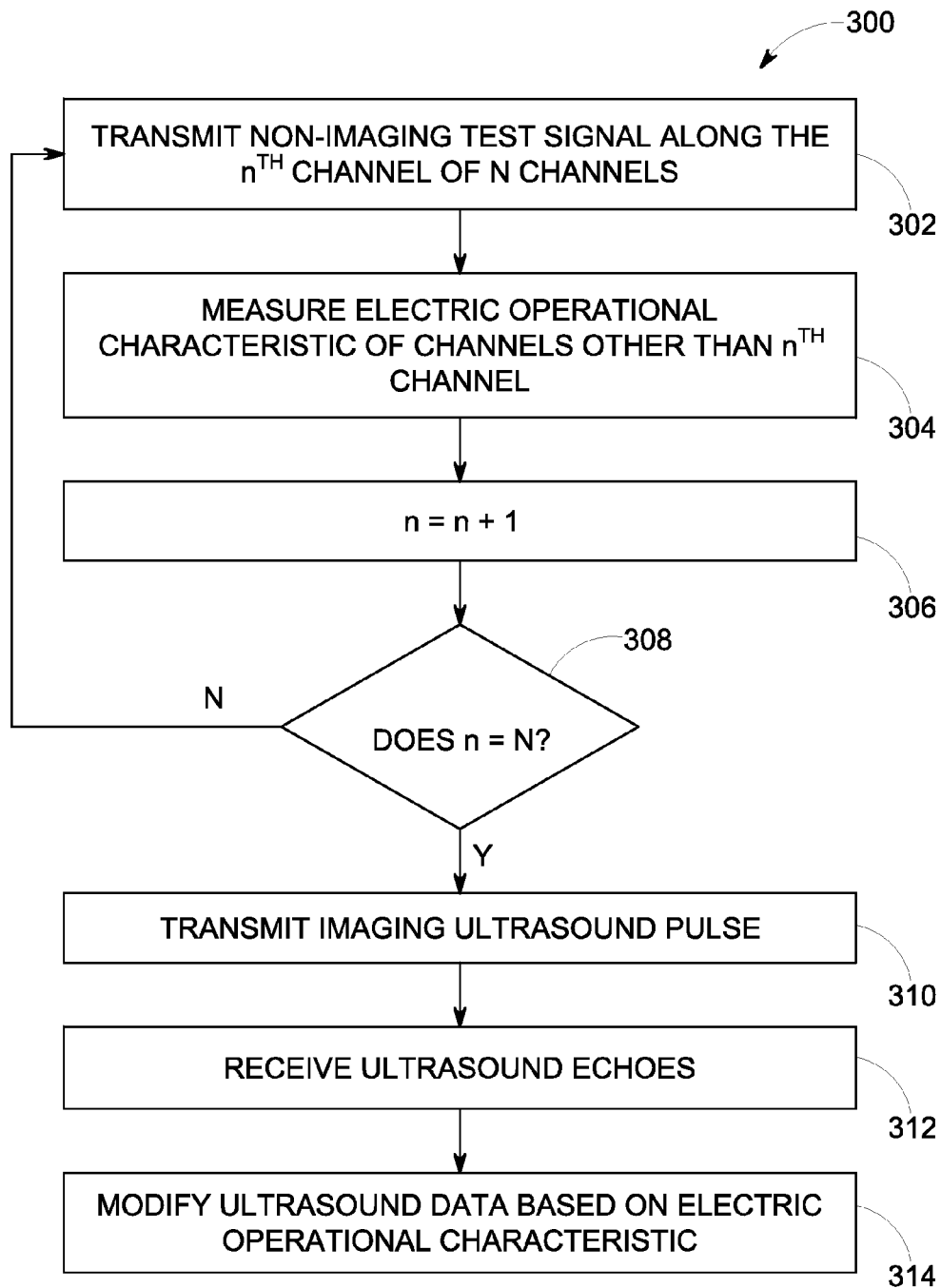
FIG. 3 is a flowchart of a method for electrically determining operational characteristics of the ultrasound system shown in FIG. 1 in accordance with one embodiment.

FIG. 3 is a flowchart of a method 300 for electrically determining electric operational characteristics of the ultrasound system 100 (shown in FIG. 1) in accordance with one embodiment. The method 300 may be used in conjunction with the ultrasound system 100 to determine an electric operational characteristic of the ultrasound system 100 and correct ultrasound data acquired by the ultrasound system 100. By way of example only, the method 300 can be employed to determine electric and/or mechanical crosstalk signals between channels over which acquired ultrasound data is communicated and to filter, correct for, reduce, eliminate, or otherwise mitigate the crosstalk between the channels. Alternatively, the method 300 may determine characteristics of the data signals communicated over the channels in order to correct for electrical deficiencies of the ultrasound system 100, such as varying time skew among the channels, manufacturing variances among the transducer elements 104 (shown in FIG. 1) that impact acquired signals, channel-to-channel variations, and the like.

At 302, a test signal is injected into at least one of the channels of the ultrasound probe 102 (shown in FIG. 1). In one embodiment, the test signal is an acoustic signal directed toward the transducer elements 104 (shown in FIG. 1). In another embodiment, the test signal is an analog electrical signal generated in the probe 102 and injected into the signal path between the transducer element 104 and the cable 110 (shown in FIG. 1). The test signal may be produced by the signal generator 220 (shown in FIG. 2).

The test signal can be iteratively transmitted each of the channels. For example, the test signal may first be transmitted along the $n^{TH}$ of N channels, where N represents the total number of channels or signal paths between the probe 102 (shown in FIG. 1) and the processing components of the ultrasound system 100 (shown in FIG. 1). As described above, the channels may represent different signal paths that include the transducer elements 104 (shown in FIG. 1), associated conductive pathways 202 (shown in FIG. 2), and other conductive bodies used to transmit ultrasound signals. Different channels represent different transducer elements 104 and the conductive pathways 202 coupled with the different transducer elements 104 in one embodiment. For example, each of a plurality of channels may communicate raw analog ultrasound data acquired by a different transducer element 104 and conveyed along a different conductive pathway 202.

Figure 4:
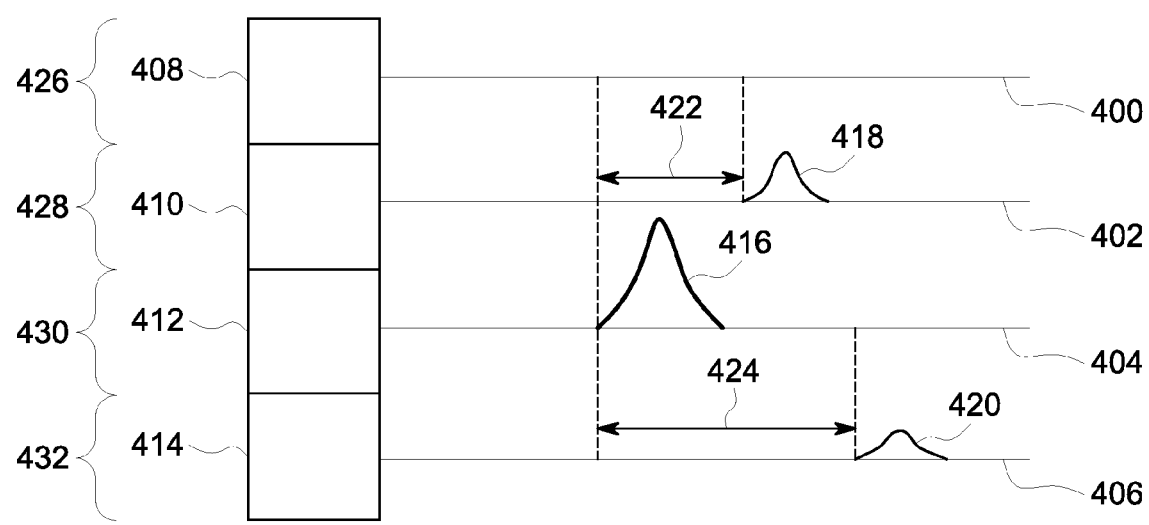
FIG. 4 is a schematic diagram of several channels and several transducer elements of the ultrasound system shown in FIG. 1 in accordance with one embodiment.

With continued reference to the method 300 shown in FIG. 3, FIG. 4 is a schematic diagram of several channels 426, 428, 430, 432 composed of several transducer elements 408, 410, 412, 414 and several conductive pathways 400, 402, 404, 406 in accordance with one embodiment. The conductive pathways 400, 402, 404, 406 represent different conductive pathways 202 (shown in FIG. 2) used to communicate acquired ultrasound data from the probe 102 (shown in FIG. 1). The transducer elements 408, 410, 412, 414 represent different transducer elements 104 (shown in FIG. 1) of the ultrasound probe 102 (shown in FIG. 1). Alternatively, one or more of the transducer elements 408, 410, 412, 414 may represent a group or set of individual transducer elements, such as a subaperture formed by a plurality of individual transducer elements. The channels 426, 428, 430, 432 include the associated transducer elements 408, 410, 412, 414 in one embodiment. While only four transducer elements 408, 410, 412, 414, four conductive pathways, 400, 402, 404, 406, and four channels 426, 428, 430, 432 are shown, alternatively a different number of transducer elements 408, 410, 412, 414, conductive pathways 400, 402, 404, 406, and/or channels 426, 428, 430, 432 may be provided. Each of the transducer elements 408, 410, 412, 414 is illustrated next to the conductive pathway 400, 402, 404, 406 that communicates the ultrasound data acquired by the transducer element 408, 410, 412, 414.

As described above, a test signal 416 may be transmitted along one or more of the channels 426, 428, 430, 432. In the illustrated embodiment, the test signal 416 is conveyed along the channel 430. As the test signal 416 propagates along the channel 430, the test signal 416 may induce a crosstalk signal in other channels 428, 432. For example, the test signal 416 may induce corresponding crosstalk signals 418, 420 in the conductive pathways 402, 406 of the channels 428, 432.

At 304 of the method 300, electric operational characteristics of one or more of the channels 426, 428, 430, 432 are determined. Electric operational characteristics may be determined for one or more channels 426, 428, 432 other than the channel 430 along which the test signal is transmitted. In the illustrated embodiment, the electric operational characteristics are determined for the channels 426, 428, 430, 432 other than the $n^{TH}$ channel. The electric operational characteristics include one or more measurements, parameters, or indices that represent signals propagating along the channels 426, 428, 430, 432. For example, an electric operational characteristic may represent an energy, voltage, frequency, or duration of a crosstalk signal 418, 420 propagating along the channel 428, 432. Alternatively, the electric operational characteristic may represent the presence of a crosstalk signal 418, 420 propagating through the channel 426, 428, 432. For example, the electric operational characteristic may be a binary representation of whether the crosstalk signal 418, 420 is conveyed through the channel 426, 428, or 432.

In another embodiment, the electric operational characteristic includes a time lag 422, 424 between the test signal 416 and the crosstalk signal 418, 420. For example, the electric operational characteristic can represent the time difference or delay between the injection of the test signal 416 on the channel 430 and the detection or appearance of the crosstalk signal 418, 420 on the channel 428 or 432.

The electric operational characteristics may be based on the frequency and/or energy of the test signal 416. For example, as the frequency and/or energy of the test signal 416 increases, the energies, voltages, frequencies, durations, and/or time lags 422, 424 of the crosstalk signals 418, 420 may change. The crosstalk signals 418, 420 may vary from channel to channel. For example, a change in the frequency and/or energy of the test signal 416 may cause different changes in each of the crosstalk signals 418, 420. As shown in FIG. 4, the test signal 416 generates different crosstalk signals 418, 420 in the different channels 428, 432.

The signals that represent non-ultrasound data (such as the crosstalk signals 418, 420) may be associated with different combinations of the channels 426, 428, 430, 432. For example, the crosstalk signal 418 may be associated with the channel 428 when a test signal 416 is transmitted along the channel 430 and the crosstalk signal 420 may be associated with the channel 432 when the test signal 416 is transmitted along the channel 430. Additional combinations of channels and the associated induced crosstalk signals (or other electric operational characteristics) may be determined. The electric operational characteristics associated with the combinations of channels 426, 428, 430, 432 may be stored in the memory 212 in a database or table that associates the electric operational characteristics (such as the crosstalk signals 418, 420) with the corresponding channels 426, 428, 430, 432. For example, the crosstalk signals that are created on induced channels when a test signal is conveyed along an inducing channel may be stored in the memory 212. The association between the inducing and induced channels may be later used to correct for the electric operational characteristics when subsequent control signals or other signals are transmitted along one or more of the channels 426, 428, 430, 432.

At 306, the method 300 incrementally proceeds to the next channel of the N channels. For example, the method 300 proceeds to the (n+1) channel and the above described process is repeated. The method 300 may repeat in order to determine the crosstalk signals generated on other channels when test signals are conveyed along each of the channels.

At 308, a determination is made as to whether a test signal has been transmitted along all of the N channels. For example, a determination is made as to whether the current channel is the $N^{TH}$ channel. If the current channel is the $N^{TH}$ channel, then the test signal has been transmitted for all N channels and the method 300 proceeds to 310. Alternatively, if the current channel is not the $N^{TH}$ channel, then the method 300 returns to 302 to transmit a test signal along the current channel. In another embodiment, the test signal is transmitted along less than all of the N channels. For example, the test signal may be transmitted along some of the N channels.

At 310, one or more imaging ultrasound pulses are transmitted by the ultrasound probe. The ultrasound system 100 (shown in FIG. 1) transmits control signals along the conductive pathways 202 (shown in FIG. 2) to the transducer elements 408, 410, 412, 414. The control signals excite the transducer elements 408, 410, 412, 414 to generate an ultrasound pulse that is emitted from the probe 102 (shown in FIG. 1). The ultrasound pulse is directed into an imaged body to generate echoes.

In one embodiment, the method 300 recursively repeats through the operations described in connection with 302, 304, 306, 308 such that the test signal is transmitted through the N channels before an ultrasound pulse is generated. Alternatively, an ultrasound pulse generated by the $n^{TH}$ channel is transmitted after the test signal is transmitted along the $n^{TH}$ channel, but before the test signal is transmitted along one or more other channels. For example, the test signal 416 may be transmitted through the channel 426, crosstalk signals are measured on the other channels 428, 430, 432, followed by transmission of control signals through the channels 426, 428, 430, 432 to generate an ultrasound pulse that is emitted from the ultrasound probe 102 (shown in FIG. 1), followed by transmission of a test signal 416 through the channel 428, followed by measuring the crosstalk signals induced on the other channels 426, 430, 432, followed by transmission of control signals to generate another ultrasound pulse, and so on. The transmission of the test signal 416 may occur shortly before transmission of the control signals, such as by 5 microseconds or less. Alternating the test signals 416 and the control signals can permit the test signals 416 to be transmitted along each channel 426, 428, 430, 432 within a single ultrasound frame or after each ultrasound frame without significantly increasing the time required to transmit the ultrasound pulses and/or receive corresponding echoes. The method 300 may provide a real-time correction or calibration of the ultrasound system 100 (shown in FIG. 1) such that electric operational characteristics (e.g., crosstalk signals and channel-to-channel variations) are determined and corrected for or removed from ultrasound data between ultrasound imaging frames during an image acquisition procedure.

At 312, echoes are received by the probe and ultrasound data is generated based on the echoes. The transducer elements 408, 410, 412, 414 receive the echoes and generate analog raw ultrasound data. The analog raw ultrasound data is conveyed along the channels 426, 428, 430, 432 as electric ultrasound signals.

At 314, the ultrasound signals conveyed along one or more of the channels 426, 428, 430, 432 is modified based on the determined electric operational characteristics, such as the previously measured crosstalk signals. The ultrasound signals may be modified based on the electric operational characteristic associated with the same transducer element 408, 410, 412, 414 that obtained the ultrasound data. The ultrasound data conveyed along the channels 426, 428, 430, 432 may be filtered to remove unwanted components, such as crosstalk signals, based on the electric operational characteristics, by the beamformer 200 (shown in FIG. 2) of the ultrasound system 100 (shown in FIG. 1) then forms an ultrasound image from the corrected ultrasound data.

The beamformer 200 can separately correct the ultrasound data conveyed along each of the channels 426, 428, 430, 432. For example, once the crosstalk signal 418, 420 is determined for each pair of the channels 426, 428, 430, 432 (with the "pair" including the inducing channel 430 and the induced channel 428 or 432), the crosstalk signals 418, 420 can be filtered from acquired ultrasound data. In the illustrated embodiment, the beamformer 200 removes or filters the crosstalk signal 418 (or a signal derived from a function based thereon) that is induced on the channel 428 by the ultrasound signal conveyed along the channel 430. The beamformer 200 repeats this correction for the other channels 426, 428, 430, 432. The beamformer 200 may remove or filter the crosstalk signal 418, 420 from acquired ultrasound data by multiplying a transfer function of the crosstalk signal 418, 420 by a scale factor and subtracting the product from the ultrasound data.

If the ultrasound system 100 (show in FIG. 1) includes N channels and the beamformer 200 receives N digitized ultrasound data signals, the beamformer 200 corrects the data conveyed along the $n^{TH}$ channel by subtracting the crosstalk signal induced on the $n^{TH}$ channel by the $i^{TH}$ channel due to the data of the $i^{TH}$ channel, the crosstalk signal induced on the $n^{TH}$ channel by the (i+1) channel, the crosstalk signal induced on the $n^{TH}$ channel by the (i+2) channel, and so on to the (N−1) channel. This process can be repeated for all N channels. For example, the above correction can be next performed for the (n+1) channel, then the (n+2) channel, and so on, for all or a subset of the N channels. If all N channels induce crosstalk signals on the other channels, then potentially there may be $(N^2-N)$ corrections made to the ultrasound data obtained for each frame. If less than all of the (N−1) channels induce crosstalk signals on the $n^{TH}$ channel, then the crosstalk signals created by less than all of the (N−1) channels may be filtered from the data of the $n^{TH}$ channel.

As described above, the measuring of the electric operational characteristics of the channels and the correction of ultrasound data conveyed along the channels may be performed during image acquisition. The injecting of test signals along the channels, measuring the electric operational characteristics of the channels based on the test signals, and the filtering of ultrasound data conveyed along the channels based on the electric operational characteristics can be repeated between transmission of ultrasound pulses from the probe 102 (shown in FIG. 1). This repeated or semi-continuous correction of the ultrasound data allows for the ultrasound data to be corrected during image acquisition, such as simultaneously or concurrently with image acquisition. In situations where the cable 110 (show in FIG. 1) is bent or flexed during image acquisition, the semi-continuous correction process can repeatedly correct the ultrasound data as the position of the cable 110 changes and the crosstalk signals or mutual impedance among the conductive pathways 202 (shown in FIG. 2) changes.

Figure 5:
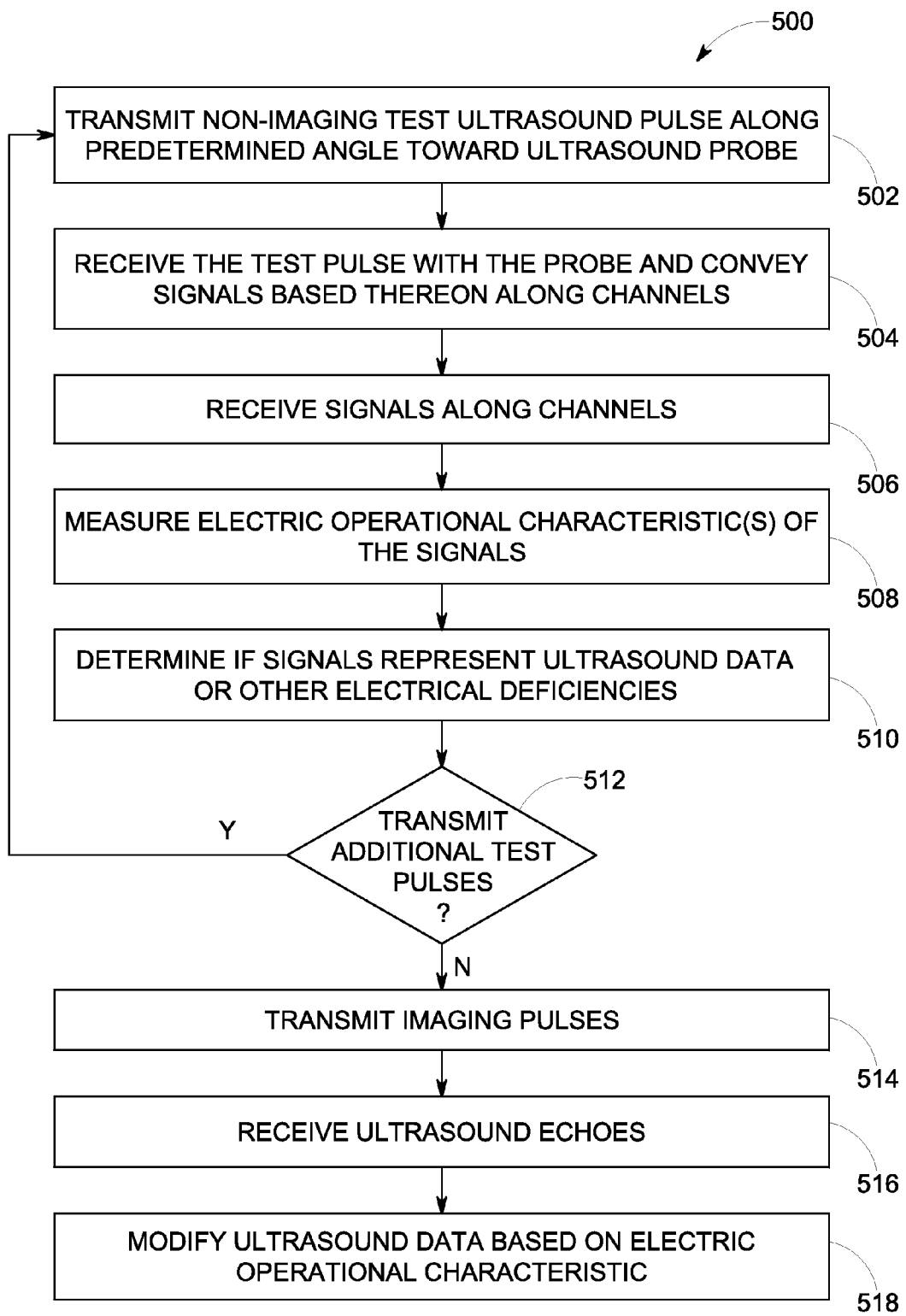
FIG. 5 is a flowchart of a method for acoustically determining operational characteristics of the ultrasound system shown in FIG. 1 in accordance with one embodiment.

FIG. 5 is a flowchart of a method 500 for acoustically determining electric operational characteristics of the ultrasound system 100 (shown in FIG. 1) in accordance with one embodiment. The method 500 may be used in conjunction with the ultrasound system 100 (shown in FIG. 1) to determine an operational characteristic of the ultrasound system 100 and correct ultrasound data acquired by the ultrasound system 100 based on the determined operational characteristic. Similar to the method 300 (shown in FIG. 3), the method 500 can be employed to determine and correct for crosstalk signals between channels of the ultrasound system 100 and/or correct for electrical deficiencies of the ultrasound system 100, such as varying time skew among the channels, manufacturing variances among the transducer elements 104 (shown in FIG. 1) that impact acquired signals, channel to channel variations, and the like. The crosstalk signals that are determined may include electric crosstalk signals (such as crosstalk signals that are induced on one pathway by transmission of ultrasound signals on another pathway) and/or mechanical crosstalk signals (such as crosstalk signals that are induced on one transducer element 104 by vibration of another transducer element 104). The ultrasound signals may be corrected by, for example, subtracting or otherwise filtering the electric and/or mechanical crosstalk signals from the ultrasound signals.

The method 500 may be used in place of or in conjunction with the method 300 (shown in FIG. 3). For example, the method 500 may be used to determine electric and/or mechanical operational characteristics of the channels prior to or after acquiring images using the ultrasound system 100 (shown in FIG. 1), such as when the ultrasound system 100 is manufactured, repaired, or rebuilt, or between image acquisitions. In contrast, the method 300 may be used during an image acquisition procedure, as described above.

At 502, a test ultrasound pulse is transmitted toward the transducer elements 104 (shown in FIG. 1) of the ultrasound probe 102 (shown in FIG. 1) along a testing direction. An external source of the ultrasound pulse is used to transmit the test pulse toward the transducer elements 104 at a predetermined angle. The pulse may be referred to as a non-imaging test pulse as the pulse is not used to generate a visual image of a body in one embodiment.

Figure 6:
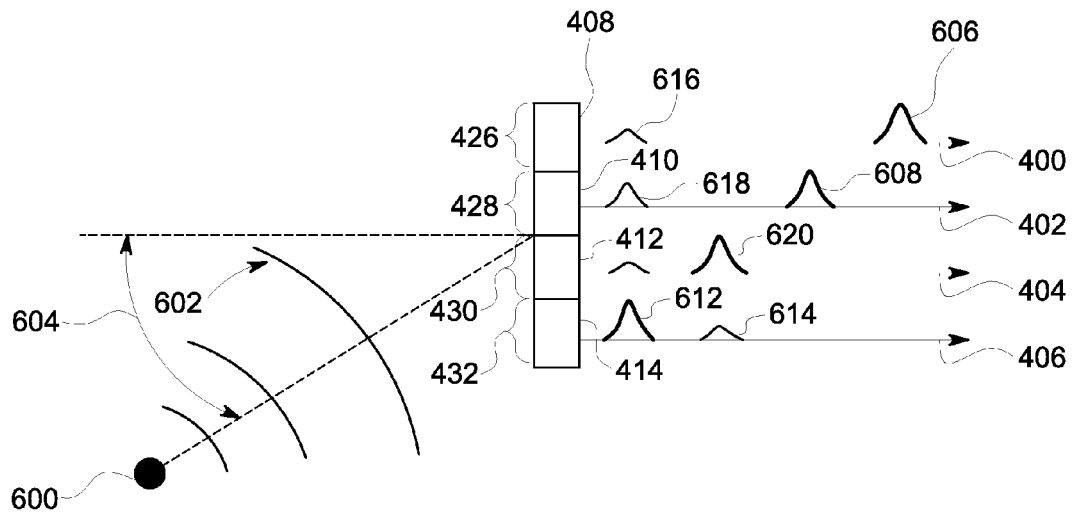
FIG. 6 is a block diagram of an external ultrasound pulse source transmitting a test pulse toward the transducer elements shown in FIG. 4 along a first testing direction in accordance with one embodiment.

With continued reference to FIG. 5, FIG. 6 is a block diagram of an external ultrasound pulse source 600 and the transducer elements 408, 410, 412, 414 in accordance with one embodiment. The pulse source 600 may be another ultrasound probe or other device capable of transmitting test pulses 602 toward the transducer elements 408, 410, 412, 414 at various angles. In the illustrated embodiment, the pulse source 600 transmits the test pulses 602 toward the transducer elements 408, 410, 412, 414 at an oblique angle 604 relative to the transducer elements 408, 410, 412, 414. The pulse source 600 and the transducer elements 408, 410, 412, 414 may be positioned within a known atmosphere, such as in a water tank, to perform at least some of the operations described in connection with the method 500.

At 504, the test pulse 602 is received by the transducer elements 408, 410, 412, 414. Depending on the location of the transducer elements 408, 410, 412, 414 and/or the angle 604, the transducer elements 408, 410, 412, 414 may receive or detect the test pulse 602 at different times. For example, the transducer elements 412, 414 that are disposed closer to the pulse source 600 may receive the test pulse 602 before the transducer elements 408, 410 located farther from the pulse source 600.

The transducer elements 408, 410, 412, 414 may vibrate during reception of the test pulse 602. The transducer elements 408, 410, 412, 414 are mechanically coupled such that the vibration of one of the transducer elements 408, 410, 412, 414 causes vibration of one or more other adjacent or nearby transducer elements 408, 410, 412, 414. The vibration of the adjacent or nearby transducer elements 408, 410, 412, 414 can create mechanical crosstalk signals on the pathways and channels of the adjacent or nearby transducer elements 408, 410, 412, 414.

The transducer elements 408, 410, 412, 414 generate raw analog ultrasound data 606, 608, 610, 612 based on the test pulse 602. The ultrasound data 606, 608, 610, 612 is conveyed along the channels 426, 428, 430, 432, as described above. The transmission of the ultrasound data 606, 608, 610, 612 through the channels 426, 428, 430, 432 and/or the vibration of one or more transducer elements 408, 410, 412, 414 induces signals on other channels 426, 428, 430, 432. For example, the ultrasound data 610 transmitted along the channel 430 induces an electric crosstalk signal 614 on the channel 432. The ultrasound data 612 transmitted along the channel 432 induces electric crosstalk signals 616, 618, 620 on the channels 426, 428, 430. In one embodiment, one or more of the crosstalk signals 616, 618, 620 includes electric and/or mechanical components. For example, one or more of the crosstalk signals 616, 618, 620 may include electric crosstalk signals and/or mechanical crosstalk signals.

At 506, the signals conveyed along the channels 426, 428, 430, 432 are received by the ultrasound system 100 (shown in FIG. 1). For example, the processor 116 (shown in FIG. 1)

may receive the ultrasound signals comprised of received analog ultrasound data along the channels 426, 428, 430, 432.

At 508, operational characteristics of the ultrasound signals conveyed along the channels 426, 428, 430, 432 are examined to determine if the ultrasound signals are representative of ultrasound data acquired from the test pulse 602 or of a deficiency in the ultrasound system 100 (shown in FIG. 1). For example, the ultrasound signals are examined to determine if the ultrasound signals represent an ultrasound echo or crosstalk signals (electric and/or mechanical crosstalk signals), bending in the cable 110 (shown in FIG. 1), time skew between the channels 426, 428, 430, 432, imperfections in the transducer elements 408, 410, 412, 414, and the like. The operational characteristics can represent differences between the signals conveyed along the channel and expected or predetermined signals. For example, the ultrasound pulse transmitted at the transducer elements 408, 410, 412, 414 may be a predetermined pulse transmitted along a predetermined angle. The predetermined pulse may be associated with signals that are expected to be received by the transducer elements 408, 410, 412, 414.

In the illustrated embodiment, the operational characteristics represent the crosstalk signals 614, 616, 618, 620. For example, the operational characteristics include one or more measurements, parameters, or indices that represent the crosstalk signals 614, 616, 618, 620, such as an energy, voltage, frequency, duration, or presence of a crosstalk signal 614, 616, 618, 620. The crosstalk signals 614, 616, 618, 620 can be induced in the channels 426, 428, 430, 432 by the ultrasound data 606, 608, 610, 612 transmitted along the channels 426, 428, 430, 432 and/or vibration of one or more transducer elements. For example, the ultrasound data 612 of the channel 432 induces the crosstalk signals 616, 618, 620 of the channels 426, 428, 430 and the ultrasound data 610 of the channel 430 induces the crosstalk signal 614 of the channel 432.

At 510, a determination is made as to whether the signals communicated along the channels 426, 428, 430, 432 represent ultrasound data or other electrical deficiencies. For example, the crosstalk signals, ultrasound data, and/or other signals conveyed along a channel are compared to one or more predetermined waveform attributes to determine if the signals and/or data represent deficiencies (such as electric and/or mechanical crosstalk) or ultrasound data. The waveform attributes are associated with an expected ultrasound signal that is based on the test pulse 602. For example, the waveform attributes may include an amplitude, frequency, energy, duration, commencement or beginning time, termination or ending time, and/or shape of a waveform segment associated with an expected signal that includes ultrasound data. The waveform attributes can be stored in the internal memory 212 (shown in FIG. 2) for comparison to the waveforms of the received signals.

Based on a comparison between the amplitude of the signal 616 and a predetermined waveform amplitude stored in the memory 212, the signal 616 may be identified as ultrasound data or crosstalk. With respect to the channel 426, the waveform attributes may include an amplitude that is greater than the amplitude of the crosstalk signal 616, but that is smaller or as least as large as the ultrasound data 606. As a result, the smaller amplitude of the crosstalk signal 616 may indicate that the crosstalk signal 616 does not represent ultrasound data associated with the test pulse 602 while the larger amplitude of the ultrasound data 606 indicates that the ultrasound data 606 represents ultrasound data associated with the test pulse 602. Alternatively, one or more other waveform attributes may be compared to each of the crosstalk signal 616 and the ultrasound data 606. Based on differences between the crosstalk signal 616 and the ultrasound data 606, the crosstalk signal 616 is identified as being representative of crosstalk while the ultrasound data 606 is identified as representative of the test pulse 602. The determination of whether signals conveyed along the channels 426, 428, 430, 432 represent electrical deficiencies or ultrasound data can be repeated for all or a subset of the channels 426, 428, 430, 432.

The signals that represent non-ultrasound data (such as the crosstalk signals 614, 616, 618, 620) may be associated with the angle 604 at which the test pulse 602 is directed toward the transducer elements 408, 410, 412, 414. For example, the crosstalk signals 614, 616, 618, 620 may be stored in the memory 212 (shown in FIG. 2) in a database or table that associates the crosstalk signals 614, 616, 618, 620 with the test pulse 602 and/or the angle 604 at which the test pulse 602 is transmitted toward the transducer elements 408, 410, 412, 414.

At 512, a determination is made as to whether additional test pulses are to be transmitted toward the ultrasound probe 102 (shown in FIG. 1). Additional ultrasound pulses may be transmitted toward the ultrasound probe 102 and the transducer elements 408, 410, 412, 414 in order to identify what electrical deficiencies, such as crosstalk signals, occur when ultrasound pulses are transmitted toward the transducer elements 408, 410, 412, 414 at other angles.

If no additional ultrasound pulses are to be transmitted toward the probe 102 (shown in FIG. 1), flow of the method 500 proceeds to 514. Alternatively, if one or more ultrasound pulses are to be transmitted toward the probe 102 (shown in FIG. 1), then flow of the method 500 returns to 502 where another ultrasound pulse is transmitted toward the probe 102 at an angle that differs from one or more previous angles at which ultrasound pulses were transmitted toward the probe 102.

Figure 7:
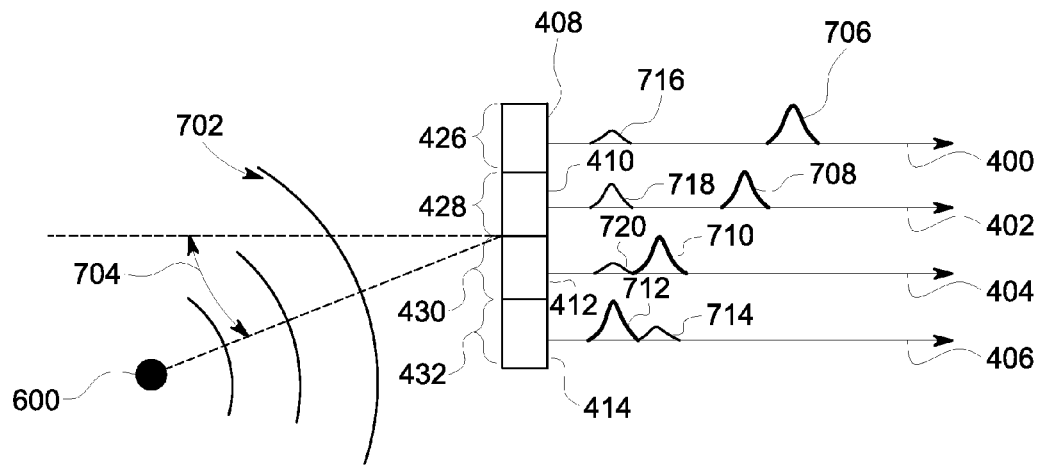
FIG. 7 is a block diagram of the external ultrasound pulse source shown in FIG. 6 transmitting another test pulse toward the transducer elements shown in FIG. 4 along a second testing direction in accordance with one embodiment.

FIG. 7 is a block diagram of the external ultrasound pulse source 600 and the transducer elements 408, 410, 412, 414 in accordance with one embodiment. As shown in FIG. 7, the pulse source 600 may transmit another non-imaging test pulse 702 toward the transducer elements 408, 410, 412, 414 along a testing direction defined by an angle 704. This additional test pulse 702 is transmitted at the angle 704 that is different than the angle 604 (shown in FIG. 6) along which the test pulse 602 was transmitted.

The test pulse 702 is received by the transducer elements 408, 410, 412, 414 and the transducer elements 408, 410, 412, 414 generate signals containing ultrasound data 706, 708, 710, 712. The ultrasound data 706, 708, 710, 712 is conveyed along the channels 426, 428, 430, 432 as ultrasound signals. Similar to as described above in connection with the test pulse 602, signals other than ultrasound data signals, such as crosstalk signals 714, 716, 718, 720, can be induced in the channels 426, 428, 430, 432 by the ultrasound data 706, 708, 710, 712 and/or by vibration of one or more transducer elements 408, 410, 412, 414. As described above, one or more waveform attributes of the crosstalk signals 714, 716, 718, 720 and/or the ultrasound data 706, 708, 710, 712 are analyzed to determine that reception of the test pulse 702 generates the crosstalk signals 714, 716, 718, 720. The crosstalk signals 714, 716, 718, 720 associated with the test pulse 702 and/or the angle 704 at which the test pulse 702 is transmitted may be stored in the memory 212 (shown in FIG. 2).

Returning to the discussion of the method 500 shown in FIG. 5, the method 500 may proceed in a loop-wise manner to collect information on operational characteristics (such as crosstalk signals) that are received, generated, or sensed by the transducer elements 408, 410, 412, 414 when ultrasound pulses are received at different angles. The set of operational characteristics associated with ultrasound pulses received at different angles is used to filter or remove non-ultrasound data signals conveyed by the channels 426, 428, 430, 432 when future ultrasound pulses are received, as described below.

At 514, one or more imaging ultrasound pulses are transmitted by the ultrasound probe. The ultrasound system 100 (shown in FIG. 1) transmits control signals along the channels 426, 428, 430, 432 to the transducer elements 408, 410, 412, 414. The control signals excite the transducer elements 408, 410, 412, 414 to generate an ultrasound pulse that is emitted from the probe 102. The ultrasound pulse is directed into an imaged body to generate echoes.

At 516, echoes are received by the probe and ultrasound data is generated based on the echoes. The transducer elements 408, 410, 412, 414 receive the echoes and generate analog raw ultrasound data. The analog raw ultrasound data is conveyed along the channels 426, 428, 430, 432.

At 518, the ultrasound data conveyed along one or more of the channels 426, 428, 430, 432 is modified based on the operational characteristics that were measured based on the test pulses 602, 702. In one embodiment, the operational characteristics that were determined when the test pulse(s) were directed at the probe 102 (shown in FIG. 1) at the same or similar angle as the imaging ultrasound pulse are subtracted or otherwise filtered from the ultrasound data. For example, if the echoes are obtained at a steering angle, then the crosstalk signals determined when test pulses were directed at the probe 102 at an angle that is the same as or approximately the same as the steering angle may be subtracted or filtered from the ultrasound data generated by the transducer elements 408, 410, 412, 414.

As described above, the measuring of the operational characteristics of the channels may be performed prior to image acquisition. The operational characteristics (such as crosstalk signals) may then be filtered from ultrasound data generated during image acquisition. In another embodiment, the operational characteristics may be determined during imaging acquisition. For example, instead of transmitting non-imaging test pulses to determine the operational characteristics prior to image acquisition, the operational characteristics may be determined using imaging ultrasound pulses. The ultrasound pulses are transmitted by the transducer elements 408, 410, 412, 414 toward an imaged body. If the approximate location and/or orientation of the imaged body relative to the ultrasound probe 102 (shown in FIG. 1) is known, then the approximate return path along which ultrasound echoes are received may be known. For example, the angle or angles along which ultrasound echoes are received may be known such that the crosstalk signals may be determined for a first imaging ultrasound pulse and used to filter the ultrasound data obtained from subsequent imaging ultrasound pulses transmitted along the same or approximately the same angle of the first imaging pulse.

In accordance with one embodiment, the selection and use of the method 300 and/or 500 (shown in FIGS. 3 and 5) may be based on how often and/or how quickly the operational characteristics of the probe 102 (shown in FIG. 1) changes. For example, if the operational characteristics of the transducer elements 408, 410, 412, 414 (shown in FIG. 4) and associated with one or more angles 604, 704 are relatively fixed or do not significantly change during use of the system 100 (shown in FIG. 1), then the method 500 may be used to initially determine the operational characteristics and correct subsequently obtained ultrasound data. If the operational characteristics change during use of the system 100 (such as by bending of the cable 110 (shown in FIG. 1)), then the method 300 may be repeatedly used during image acquisition. In another embodiment, both the method 300 and the method 500 are used to correct ultrasound data to remove unwanted operational characteristics.

In one embodiment, the method 500 (shown in FIG. 5) may be used to obtain a database of operational characteristics associated with the channels of a type or category of ultrasound probe. This database may be replicated and uploaded to the memory 212 (shown in FIG. 2) for each of a set of probes that are the same or similar type of ultrasound probe. The database may be used to calibrate the same type of probes. For example, once the database is established, the database may be downloaded to the internal memories 212 of other similar types of probes 102 and used by the similar probes 102 to correct for crosstalk signals. Ultrasound probes 102 may be similar or the same type based on the geometry, size, composition, and the like of the probes 102. Alternatively, the method 500 may be used to obtain the database for each of several probes. For example, prior to ever using a probe to image a body (or periodically during the service life of the probe), the method 500 may be used to generate or update the database. The probe may then refer to the database to filter or reduce unwanted operational characteristics (such as crosstalk signals) from received ultrasound data.

In another embodiment, a simulation model of crosstalk signals may be generated. For example, the crosstalk signals that are induced on channels by ultrasound signals conveyed along another channel may be modeled or approximated without physically measuring crosstalk signals conveyed along any channel. The simulation model may be a computer-generated model that associates expected crosstalk signals that are induced on the channels of an ultrasound system when ultrasound signals are conveyed along the channels. The model is downloaded to the memories 212 (shown in FIG. 2) of the ultrasound systems 100 (shown in FIG. 1) and used to subtract or remove the crosstalk signals from subsequently acquired ultrasound signals.

In one embodiment, the crosstalk signals that are determined for one or more of the channels may be used to modify control or transmit signals. For example, the crosstalk signals may be used to modify the control signals that are conveyed to the transducer elements of the ultrasound probe in order to cause the transducer elements to emit one or more ultrasound pulses. The control signal for one or more channels may be determined and the previously determined crosstalk signal(s) for the one or more channels may be removed, filtered, or subtracted from the control signals prior to communicating the control signals along the channels.

Figure 8:
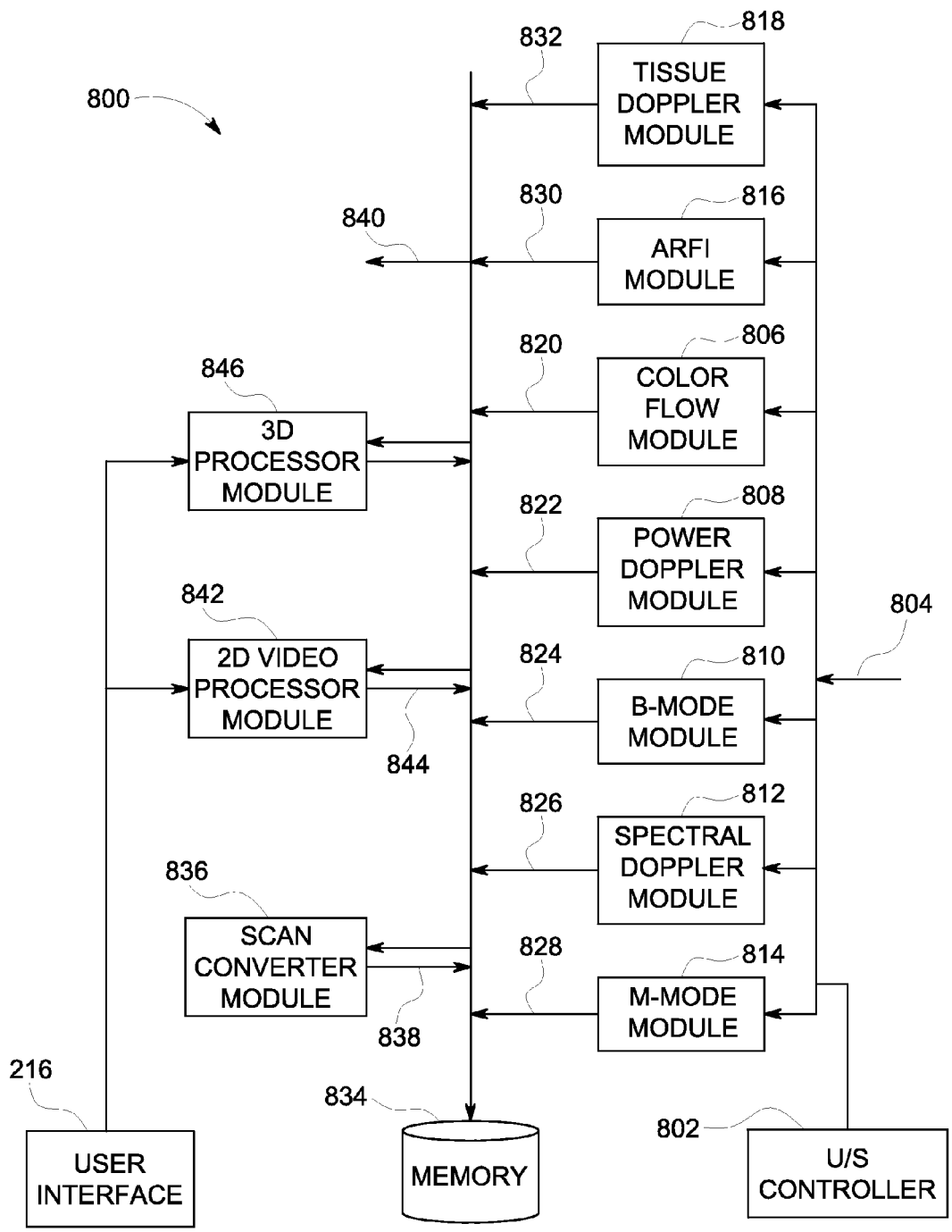
FIG. 8 illustrates an exemplary block diagram of an ultrasound processor module in accordance with one embodiment.

FIG. 8 illustrates an exemplary block diagram of an ultrasound processor module 800, which may be embodied as the processor 116 of FIG. 1 or a portion thereof. The ultrasound processor module 800 is illustrated conceptually as a collection of sub-modules, but may be implemented utilizing any combination of dedicated hardware boards, DSPs, processors, etc. Alternatively, the sub-modules of FIG. 8 may be implemented utilizing an off-the-shelf PC with a single processor or multiple processors, with the functional operations distributed between the processors. As a further option, the sub-modules of FIG. 8 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules illustrated in FIG. 8 may be controlled by a local ultrasound controller 802 or by the processor module 800. The processor module 800 may receive ultrasound data 804 in one of several forms. The ultrasound data 804 may include the ultrasound data 606, 608, 610, 612, 706, 708, 710, 712 (shown in FIGS. 4, 6, and 7). In the embodiment of FIG. 8, the received ultrasound data 804 constitutes I,Q data pairs representing the real and imaginary components associated with each data sample. The I,Q data pairs are provided to one or more of a color-flow module or sub-module 806, a power Doppler module or sub-module 808, a B-mode module or sub-module 810, a spectral Doppler module or sub-module 812 and an M-mode module or sub-module 814. Optionally, other sub-modules may be included such as an Acoustic Radiation Force Impulse (ARFI) module or sub-module 816 and a Tissue Doppler (TDE) module or sub-module 818, among others.

Each of the sub-modules 806, 808, 810, 812, 814, 816, 818 are configured to process the I,Q data pairs in a corresponding manner to generate color-flow data 820, power Doppler data 822, B-mode data 824, spectral Doppler data 826, M-mode data 828, ARFI data 830, and tissue Doppler data 832, all of which may be stored in a memory 834 (such as the memory 212 and/or 218 shown in FIG. 2) temporarily before subsequent processing. For example, the B-mode sub-module 810 may generate B-mode data 824 including a plurality of B-mode image planes, such as in a biplane or triplane image acquisition as described in more detail herein. The data 820, 822, 824, 826, 828, 830, 832 may be stored, for example, as sets of vector data values, where each set defines an individual ultrasound image frame. The vector data values are generally organized based on the polar coordinate system. Alternatively, the ultrasound data 804 may be transmitted to a beamformer, such as the software beamformer 200 (shown in FIG. 2), prior to being processed by one or more of the sub-modules 806, 808, 810, 812, 814, 816, 818.

A scan converter module or sub-module 836 accesses and obtains from the memory 834 the vector data values associated with an image frame and converts the set of vector data values to Cartesian coordinates to generate an ultrasound image frame 838 formatted for display. The ultrasound image frames 838 generated by the scan converter sub-module 836 may be provided back to the memory 834 for subsequent processing. Once the scan converter sub-module 836 generates the ultrasound image frames 838 associated with, for example, B-mode image data, and the like, the image frames may be restored in the memory 834 or communicated over a bus 840 to a database (not shown), the memory 834, and/or to other processors.

The scan converted data may be converted into an X,Y format for video display to produce ultrasound image frames. The scan converted ultrasound image frames are provided to a display controller (not shown) that may include a video processor that maps the video to a grey-scale mapping for video display. The grey-scale map may represent a transfer function of the raw image data to displayed grey levels. Once the video data is mapped to the grey-scale values, the display controller controls the display device 214 (shown in FIG. 2), which may include one or more monitors or windows of the display, to display the image frame. The image displayed in the display device 214 is produced from image frames of data in which each datum indicates the intensity or brightness of a respective pixel in the display.

A 2D video processor module or sub-module 842 combines one or more of the frames generated from the different types of ultrasound information. For example, the 2D video processor sub-module 842 may combine a different image frames by mapping one type of data to a grey map and mapping the other type of data to a color map for video display. In the final displayed image, color pixel data may be superimposed on the grey scale pixel data to form a single multi-mode image frame 844 (e.g., functional image) that is again restored in the memory 834 or communicated over the bus 840. Successive frames of images may be stored as a cine loop in the memory 834. The cine loop represents a first in, first out circular image buffer to capture image data that is displayed to the user. The user may freeze the cine loop by entering a freeze command at the user interface 216. The user interface 216 may include, for example, a keyboard and mouse and all other input controls associated with inputting information into the ultrasound system 100 (shown in FIG. 1).

A 3D processor module or sub-module 846 is also controlled by the user interface 216 and accesses the memory 834 to obtain 3D ultrasound image data and to generate three dimensional images, such as through volume rendering or surface rendering algorithms as are known. The three dimensional images may be generated utilizing various imaging techniques, such as ray-casting, maximum intensity pixel projection and the like.

Figure 9:
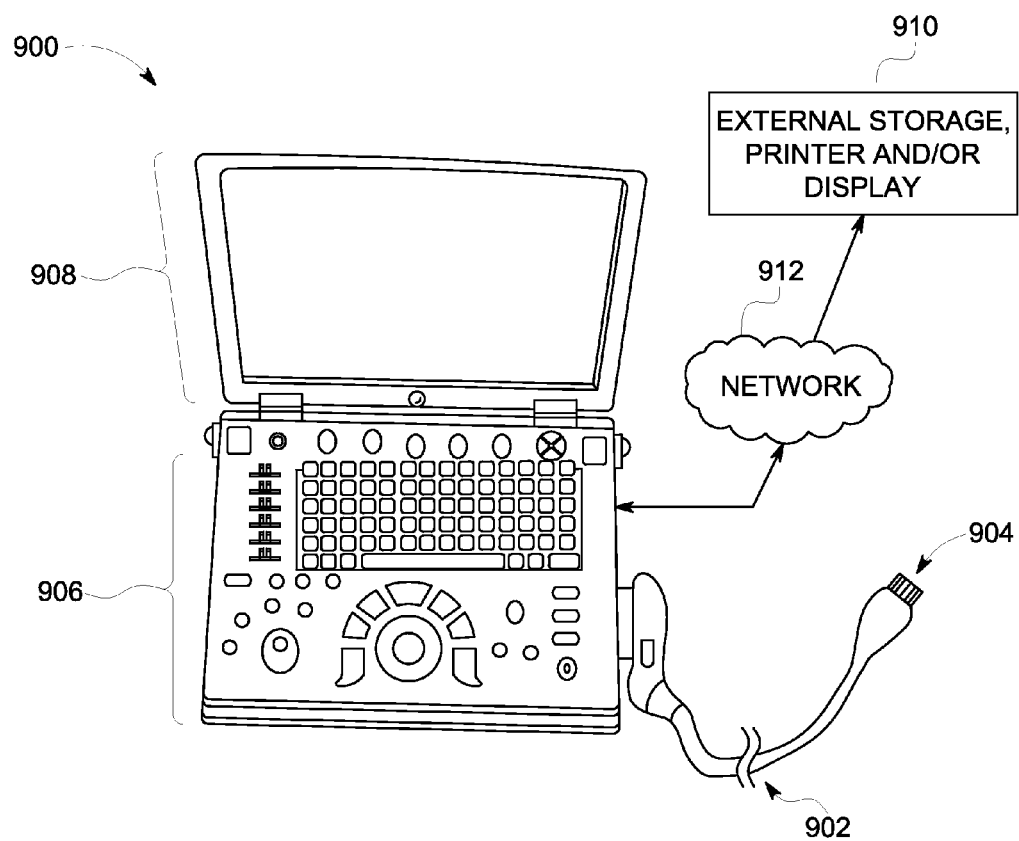
FIG. 9 illustrates a 3D-capable miniaturized ultrasound system in accordance with one embodiment.
Figure 10:
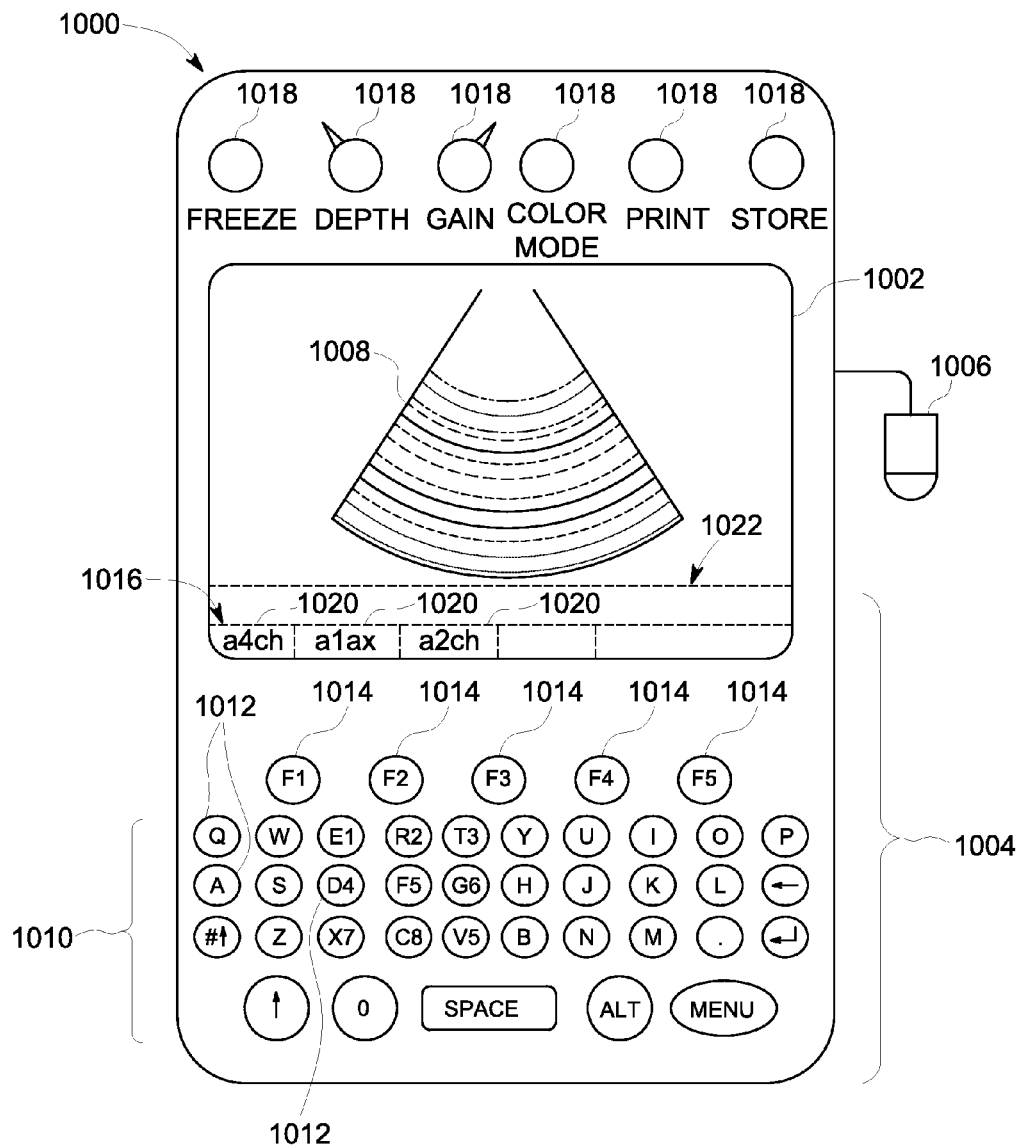
FIG. 10 illustrates a hand carried or pocket-sized ultrasound imaging system in accordance with one embodiment.
Figure 11:
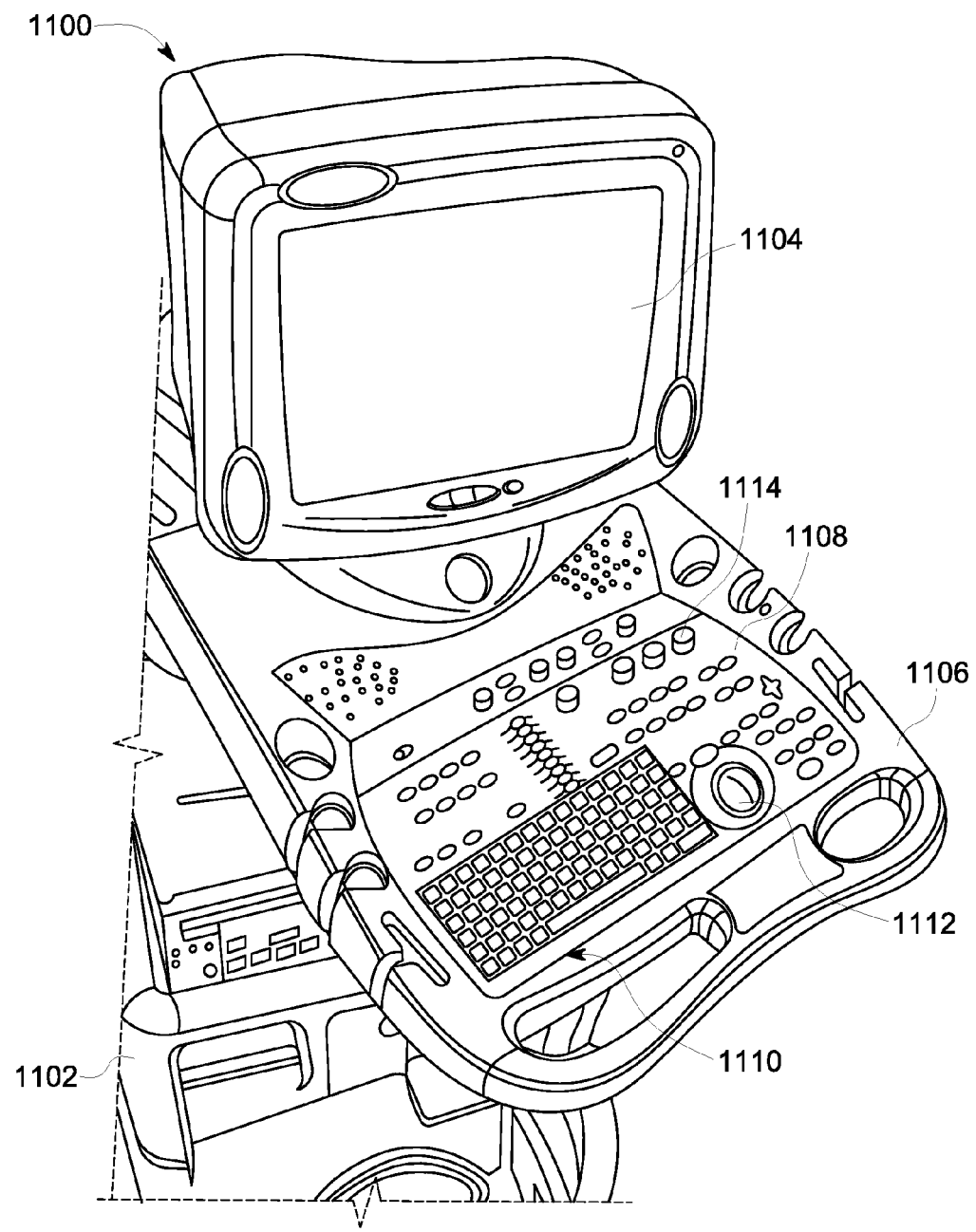
FIG. 11 illustrates an ultrasound imaging system in accordance with another embodiment.

The ultrasound system 100 of FIG. 1 may be embodied in a small-sized system, such as laptop computer or pocket sized system as well as in a larger console-type system. FIGS. 9 and 10 illustrate small-sized systems, while FIG. 11 illustrates a larger system.

FIG. 9 illustrates a 3D-capable miniaturized ultrasound system 900 having a probe 902 that may be configured to acquire 3D ultrasonic data or multi-plane ultrasonic data. For example, the probe 902 may have a 2D array of transducer elements 904 as discussed previously with respect to the probe 102 of FIG. 1 and the transducer elements 408, 410, 412, 414 shown in FIG. 4. A user interface 906 (that may also include an integrated display device 908) is provided to receive commands from an operator. As used herein, "miniaturized" means that the ultrasound system 900 is a handheld or hand-carried device or is configured to be carried in a person's hand, pocket, briefcase-sized case, or backpack. For example, the ultrasound system 900 may be a hand-carried device having a size of a typical laptop computer. The ultrasound system 900 is easily portable by the operator. The integrated display device 908 (e.g., an internal display) is configured to display, for example, one or more medical images.

The ultrasonic data may be sent to an external device 910 via a wired or wireless network 912 (or direct connection, for example, via a serial or parallel cable or USB port). In some embodiments, the external device 910 may be a computer or a workstation having a display, or the DVR of the various embodiments. Alternatively, the external device 910 may be a separate external display or a printer capable of receiving image data from the hand carried ultrasound system 900 and of displaying or printing images that may have greater resolution than the integrated display device 908.

FIG. 10 illustrates a hand carried or pocket-sized ultrasound imaging system 1000 wherein a display device 1002 and a user interface 1004 form a single body or unit. By way of example, the pocket-sized ultrasound imaging system 1000 may be a pocket-sized or hand-sized ultrasound system approximately 2 inches wide, approximately 4 inches in length, and approximately 0.5 inches in depth and weighs less than 3 ounces. The pocket-sized ultrasound imaging system 1000 generally includes the display device 1002, the user interface 1004, which may or may not include a keyboard-type interface and an input/output (I/O) port for connection to a scanning device, for example, an ultrasound probe 1006. The display device 1002 may be, for example, a 320×320 pixel color LCD display (on which a medical image 1008 may be displayed). A typewriter-like keyboard 1010 of buttons 1012 may optionally be included in the user interface 1004.

Multi-function controls 1014 may each be assigned functions in accordance with the mode of system operation (e.g., displaying different views). Therefore, each of the multi-function controls 1014 may be configured to provide a plurality of different actions. Label display areas 1016 associated with the multi-function controls 1014 may be included as necessary on the display device 1002. The system 1000 may also have additional keys and/or controls 1018 for special purpose functions, which may include, but are not limited to "freeze," "depth control," "gain control," "color-mode," "print," and "store."

One or more of the label display areas 1016 may include labels 1020 to indicate the view being displayed or allow a user to select a different view of the imaged object to display. The selection of different views also may be provided through the associated multi-function control 1014. The display device 1002 may also have a textual display area 1022 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 1000 and the miniaturized ultrasound system 900 may provide the same scanning and processing functionality as the system 100 (shown in FIG. 1).

FIG. 11 illustrates an ultrasound imaging system 1100 provided on a movable base 1102. The portable ultrasound imaging system 1100 may also be referred to as a cart-based system. A display device 1104 and user interface 1106 are provided and it should be understood that the display device 1104 may be separate or separable from the user interface 1106. The user interface 1106 may optionally be a touchscreen, allowing the operator to select options by touching displayed graphics, icons, and the like.

The user interface 1106 also includes control buttons 1108 that may be used to control the portable ultrasound imaging system 1100 as desired or needed, and/or as typically provided. The user interface 1106 provides multiple interface options that the user may physically manipulate to interact with ultrasound data and other data that may be displayed, as well as to input information and set and change scanning parameters and viewing angles, etc. For example, a keyboard 1110, trackball 1112, and/or multi-function controls 1114 may be provided.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for correcting ultrasound data, the method comprising:
    acquiring ultrasound data using an ultrasound probe having a plurality of transducer elements associated with a plurality of channels that include conductive pathways during an image acquisition procedure;
    communicating the ultrasound data as received ultrasound signals along the conductive pathways of the channels;
    measuring electrical operational characteristics of one or more of the channels during an image acquisition procedure; and
    determining a crosstalk signal that is generated in one or more of the channels by at least one of communication of the received ultrasound signals along the channels or vibration of one or more of the transducer elements based on the electrical operational characteristics.

2. The method of claim 1, further comprising transmitting an ultrasound pulse from the ultrasound probe during the image acquisition procedure, receiving one or more subsequently acquired ultrasound signals, and modifying one or more of the subsequently acquired ultrasound signals based on the crosstalk signal.

3. The method of claim 1, wherein an inducing channel of the channels creates the crosstalk signal on a different, induced channel of the channels based on communication of the ultrasound signals, the inducing channel and the induced channel including separate channels having electrically separate conductive pathways.

4. The method of claim 1, wherein the measuring includes transmitting a test signal along an inducing channel of the channels and the determining includes identifying the crosstalk signal that is created in an induced channel of the channels, the inducing and induced channels being electrically separate channels.

5. The method of claim 4, further comprising transmitting imaging ultrasound pulses from the ultrasound probe to image a body during the image acquisition procedure, wherein the measuring and determining operations occur between transmissions of the imaging ultrasound pulses.

6. The method of claim 1, wherein the measuring operation includes receiving an ultrasound echo at the ultrasound probe, generating a received ultrasound signal based on the ultrasound echo, communicating the received ultrasound signal along an inducing channel of the plurality of channels, and the determining operation includes acoustically determining, based on the electrical operational characteristics, a mechanical component of the crosstalk signal that is created on an induced channel of the plurality of channels by vibration of one or more of the transducer elements.

7. The method of claim 6, wherein the measuring operation includes transmitting a plurality of the ultrasound echoes toward the ultrasound probe at a plurality of different angles and determining a plurality of the crosstalk signals for one or more of the channels at the plurality of different angles.

8. The method of claim 1, wherein the determining includes determining the crosstalk signal based on a simulation model of ultrasound echoes received by the ultrasound probe and based on the ultrasound signals communicated along the conductive pathways and based on the ultrasound echoes.

9. The method of claim 1, further comprising conveying transmit signals to the ultrasound probe and transmitting ultrasound pulses from the ultrasound probe based on the transmit signals, the transmit signals modified based on the crosstalk signals.

10. The method of claim 1, wherein the determining includes determining the crosstalk signal for the ultrasound probe based on a type of ultrasound probe.

11. An ultrasound system comprising:
    an ultrasound probe configured to acquire ultrasound echoes and transmit ultrasound signals based on the ultrasound echoes during an imaging acquisition procedure;
    a plurality of channels associated with the ultrasound probe, the channels including conductive pathways configured to communicate the ultrasound signals; and
    a processor communicatively coupled with the channels, the processor measuring electrical operational characteristics of one or more of the channels during the image acquisition procedure, the processor monitoring the channels to determine a crosstalk signal that is induced on one or more of the conductive pathways of the channels by communication of the ultrasound signals along the conductive pathways based on the electrical operational characteristics.

12. The system of claim 11, wherein the ultrasound probe is configured to transmit an ultrasound pulse and receive one or more subsequently acquired ultrasound signals during the image acquisition procedure, the processor configured to modify one or more of the subsequently acquired ultrasound signals based on the crosstalk signal.

13. The system of claim 11, wherein the plurality of channels includes an inducing channel and a separate induced channel, the inducing channel creating the crosstalk signal on the induced channel by communication of one or more of the ultrasound signals along the inducing channel.

14. The system of claim 11, further comprising a signal generator configured to inject a test signal on one or more of the channels, the processor electrically determining the crosstalk signal by monitoring the channels to determine the crosstalk signal that is induced on one or more of the channels by the test signal.

15. The system of claim 11, wherein the processor acoustically determines the crosstalk signal by monitoring the channels after the ultrasound probe receives an externally generated ultrasound probe to determine the crosstalk signal that is induced on one or more of the channels by the externally generated ultrasound probe.

16. A tangible computer readable storage medium for an ultrasound system having a processor and an ultrasound probe associated with a plurality of channels over which ultrasound signals are communicated, the computer readable storage medium including:
    instructions to direct the ultrasound probe to acquire ultrasound data and communicate the ultrasound data along the channels as ultrasound signals during an image acquisition procedure; and
    instructions to direct the processor to measure electrical operational characteristics of one or more of the channels during an image acquisition procedure and to determine a crosstalk signal that is induced on one or more conductive pathways associated with the channels by communication of the ultrasound signals along the conductive pathways based on the electrical operational characteristics.

17. The computer readable storage medium of claim 16, wherein the instructions direct the processor to direct the ultrasound probe to transmit an ultrasound pulse and receive one or more subsequently acquired ultrasound pulses during the image acquisition procedure, the processor further directed to modify one or more of the subsequently acquired ultrasound signals based on the crosstalk signal.

18. The computer readable storage medium of claim 16, wherein the instructions direct the processor to determine the crosstalk signal by causing a signal generator of the ultrasound system to inject a test signal along an inducing channel of the plurality of channels and identify the crosstalk signal that is created on a separate induced channel.

19. The computer readable storage medium of claim 16, wherein the instructions direct the processor to determine the crosstalk signal by monitoring the conductive pathways when an externally generated ultrasound pulse is received by the ultrasound probe and determining the crosstalk signal that is generated on one or more of the conductive pathways by the ultrasound signals based on the externally generated ultrasound pulse.

20. The computer readable storage medium of claim 16, wherein the instructions direct the processor to determine the crosstalk signal based on a simulation model of the ultrasound probe and the channels.

* * * * *